United States Patent [19]

Shibatani et al.

[11] Patent Number: 5,378,627
[45] Date of Patent: Jan. 3, 1995

[54] PROCESS FOR PREPARING (2S,3R)-3-ALKYL-PHENYLGLYCIDIC ACID ESTERS USING LIPASE

[75] Inventors: Takeji Shibatani; Hiroaki Matsumae, both of Kobe; Eri Kawai, Kyoto, all of Japan

[73] Assignee: Tanabe Seiyaku Co., Ltd., Osaka, Japan

[21] Appl. No.: 926,617

[22] Filed: Aug. 10, 1992

[30] Foreign Application Priority Data

Aug. 13, 1991 [JP] Japan ................... 3-288245

[51] Int. Cl.$^6$ .................... C12P 41/00; C12N 1/00
[52] U.S. Cl. .................... 435/280; 435/874; 435/880; 435/921; 435/931; 435/939
[58] Field of Search .............. 435/280, 874, 880, 921, 435/931, 939

[56] References Cited

FOREIGN PATENT DOCUMENTS 0206436 12/1986 European Pat. Off. .
0343714 11/1989 European Pat. Off. .
0417785  9/1990 European Pat. Off. .
4115697 11/1991 Germany .
90/04643  5/1990 WIPO .

OTHER PUBLICATIONS

Kirchner G. et al., J. Am. Chem. Soc. 107:7072–76 (1985).
Baratti J. et al., Proc World Conf Emerging Technol Fats Oils Ind eds Baldwin, Am Oil Chem. pp. 355–358 (1985).
Chemical Abstracts 115:134224 (1991).

Primary Examiner—Douglas W. Robinson
Assistant Examiner—S. Saucier
Attorney, Agent, or Firm—Browdy and Neimark

[57] ABSTRACT

A process for preparing optically active 3-phenylglycidic acid esters comprising reacting a racemic trans-3-phenylglycidic acid with an alkanol in the presence of a hydrolase to esterify preferentially either (2S, 3R) isomer or (2R, 3S) isomer of said racemic compound and isolating and collecting the resulting optically active 3-phenylglycidic acid ester from the reaction mixture, whereby the optically active ester can be produced in a single step and in a highly pure form. The optically active 3-phenylglycidic acid esters are useful for the preparation of 1,5-benzothiazepine derivatives having pharmacological activities such as platelet aggregation inhibitory activity.

5 Claims, 3 Drawing Sheets

PROCESS FOR PREPARING (2S,3R)-3-ALKYL-PHENYLGLYCIDIC ACID ESTERS USING LIPASE

This invention relates to a process for preparing optically active 3-phenylglycidic acid esters.

BACKGROUND OF THE INVENTION

It is known that 3-phenylglycidic acid esters are useful as an intermediate for preparing 1,5-benzothiazepine derivatives having pharmacological activities such as platelet aggregation inhibitory activity (U.S. Pat. No. 4,590,188).

It is also known that optically active 3-phenylglycidic acid ester compound can be prepared by permitting a culture broth, cells or treated cells of as microoganisms having an ability of stereoselectively hydrolyzing a (2R, 3S)-3-phenylglycidic acid ester compound to act on a racemic 3-phenylglycidic acid ester compound which may also have a substituent on the phenyl group, thereby hydrolyzing the (2R, 3S) optically active isomer and separating and collecting the (2R, 3S) antipode from the reaction mixture (European Patent Publication No. 417785).

BRIEF SUMMARY OF THE INVENTION

In order to obtain an improved process for preparing optically active 3-phenylglycidic acid esters the present inventors have intensively investigated and have found that a symmetrical hydrolase produced by a microorganism such as a species of the genus Candida has an ability of producing optically active 3-phenylglycidic acid esters from racemic trans-3-phenylglycidic acid and the desired optically active 3-phenylglycidic acid esters can be obtained by utilizing said enzyme.

An object of this invention is to provide an industrially advantageous process for preparing optically active 3-phenylglycidic acid esters which are useful as an intermediate for preparing optically active , 1,5-benzothiazepine derivatives. Another object of the invention is to provide an improved process for preparing the 3-phenylglycidic acid esters utilizing an hydrolase produced by a microorganism. These and other objects and advantages of the invention will be apparent to those skilled in the art from the following description.

BRIEF DESCRIPTION OF THE DRAWING

The accompanying

The accompanying

The accompanying

DETAILED DESCRIPTION OF THE INVENTION

Figure 1:
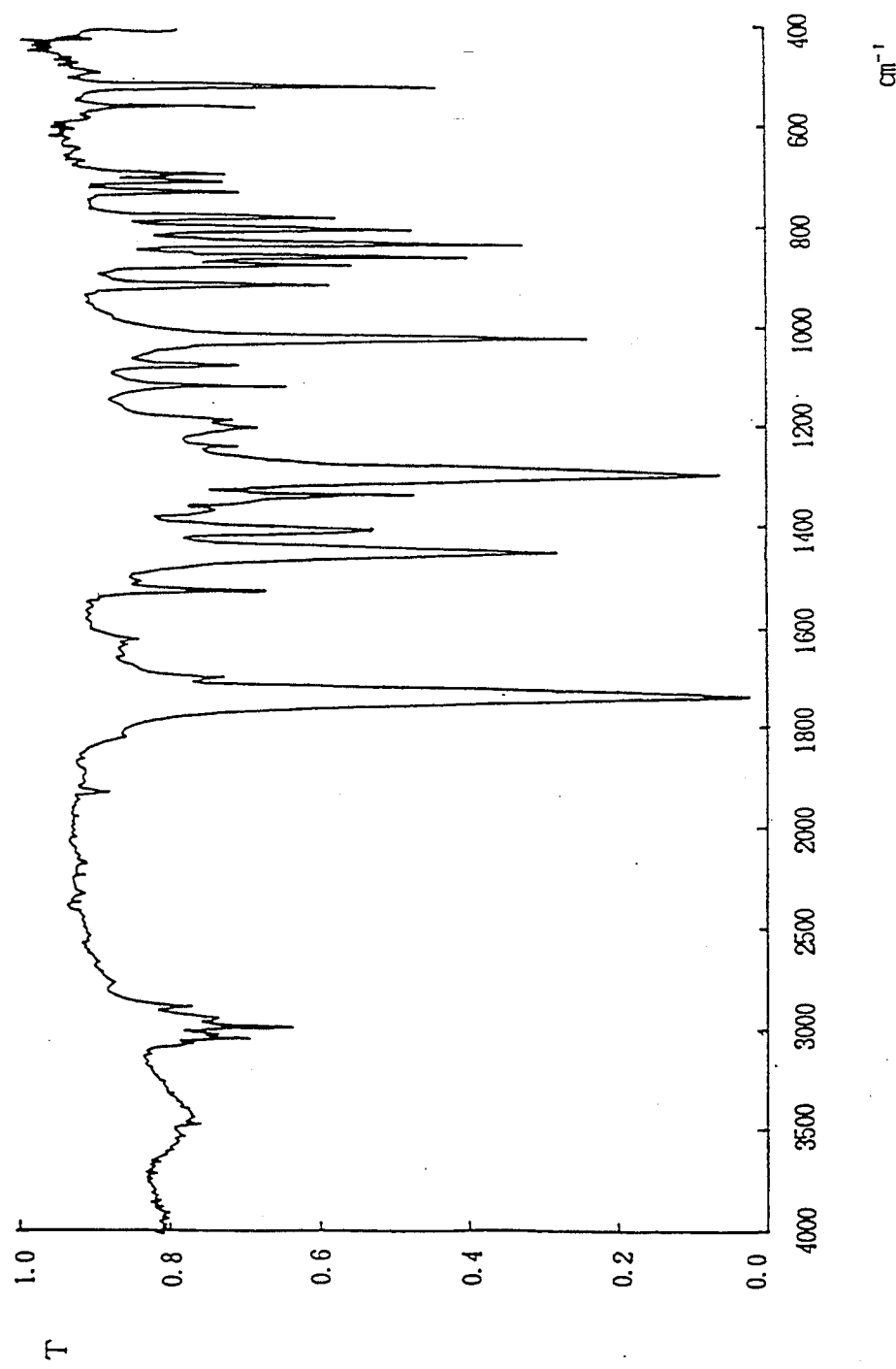
FIG. 1 shows IR spectrum (KBr) of (2S, 3R)-3-(4-methylphenyl)glycidic acid methyl ester obtained in Example 1.

This invention provides a process for preparing an optically active 3-phenylglycidic acid ester of the formula:

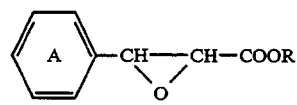

(I)

wherein the ring A is a phenyl ring which may optionally have a substituent and R is an alkyl group, which comprises reacting a racemic trans-3-phenylglycidic acid of the formula:

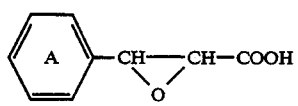

(II)

wherein the ring A is as defined above, with an alkanol in the presence of a hydrolase to esterify preferentially either (2S, 3R) isomer or (2R, 3S) isomer of said compound (II) and isolating and collecting the resulting optically active 3-phenylglycidic acid ester (1) from the reaction mixture.

The starting racemic trans-3-phenylglycidic acid (II) may optionally have a substituent selected from a lower alkyl, a lower alkoxy and a halogen atom. Suitable examples of the substituent are 4-methyl, 4-methoxy or 4-chloro. The starting compound is a mixture of (2S, 3R) isomer and (2R, 3S) isomer, but the mixing ratio is not specified, that is, inclusive not only equivalent ratio but also any other mixing ratios. Another starting alkanol is preferably alkanols having 1 to 8 carbon atoms, for example, methyl alcohol, ethyl alcohol, n-propyl alcohol, n-amyl alcohol, and n-octyl alcohol.

The hydrolase useful in this invention includes any enzyme which has an ability of asymmetrically esterifying the starting 3-phenylglycidic acid, preferentially either (2S, 3R) isomer or (2R, 3S) isomer thereof. The enzyme having such an ability includes hydrolases produced by microorganisms, for example, yeasts of the genus Candida, moulds of the genus Mucor or Rhizopus, bacteria of the genus Pseudomonas, Achromobacter, Chromobacterium, or Serratia. Specific examples of the enzyme are lipase and esterase which are produced by *Candida cylindracea, Chromobacterium viscosum, Mucor javanicus, Mucor miehei, Rhizopus chinensis, Rhizopus arrhizus,* Pseudomonas sp., *Serratia marcescens,* and the like.

The above enzymes may be obtained by extracting enzymes from cultured broths of the microorganisms, followed by purifying the extract by a conventional method, or some of them are commercially available. The commercially available enzymes are Lipase OF (origin: *Candida cylindracea,* manufactured by Meito Sangyo Co., Ltd., Japan), alkaline lipase (origin: Achromobacter sp., manufactured by Wako Pure Chemical Industries, Ltd., Japan), Lipase MY (origin: *Candida cylindracea,* manufactured by Meito Sangyo Co., Ltd., Japan), Lipase AY (origin: *Candida cylindracea,* manufactured by Amano Pharmaceutical Co., Ltd., Japan), Lipase LP (origin: *Chromobacterium viscosum,* manufactured by Toyo Jozo Co., Ltd., Japan), Lipase B (origin: *Pseudomonas fragi* 22–39B, manufactured by Wako Pure Chemical Industries, Ltd., Japan), Lipase M (origin: *Mucor javanicus,* manufactured by Amano Pharmaceutical Co., Ltd., Japan), Esterase (origin: *Mucor miehei,* manufactured by Gist, France), Lipase type XI (origin: *Rhizopus arrhizus,* manufactured by Sigma Chemical Co., U.S.A.), lipase (origin: *Rhizopus chinensis*, manufactured by Snow Brand Milk Products Co., Ltd., Japan), Lipase CES (origin: Pseudomonas sp., manufactured by Amano Pharmaceutical Co., Ltd., Japan), Lipase type XII (origin: *Candida cylindracea*, manufactured by Sigma Chemical Co., U.S.A.), Lipase YS (origin: Pseudomonas sp., manufactured by Amano Pharmaceutical Co., Ltd., Japan), and the like.

The hydrolases in this invention may be used in the immobilized form prepared by a conventional method, such as a polyacrylamide method, a gelling method with polysaccharides containing sulfur (gelling method with carrageenan, etc.), a gelling method with alginic acid, a gelling method with agar, with photo-crosslinkable resins, with polyethylene glycol, and the like.

The asymmetric esterification in this invention can be carried out by treating the racemic 3-phenylglycidic acid (II) and the alkanol with the hydrolase in an organic solvent. The substrate racemic 3-phenylglycidic acid (II) is used in a concentration of about 0.25 to 10 % by weight, preferably 0.5 to 2.5% by weight, and the compound (II) and another substrate alkanol are used in a molar ratio of 1:1 to 1:0.25, preferably 1:1 to 1:0.5. The substrate alkanol is used in a concentration of about 0.01 to 2.5% by volume, preferably 0.05 to 0.6% by volume. The reaction is usually carried out at room temperature or at an elevated temperature, preferably about 20° to 50° C., more preferably about 30° to 40° C.

The organic solvent used in the above reaction is preferably a solvent which can dissolve the 3-phenylglycidic acid esters (I) but is substantially immiscible with water. Suitable examples of the solvent are toluene, xylene, carbon tetrachloride, benzene, trichloroethane, hexane, cyclohexane, heptane, isooctane, trichloroethylene, chloroform, ethyl acetate, butyl acetate, octyl alcohol, methyl isobutyl ketone, t-butyl methyl ether, diisopropyl ether, and the like, among which preferred ones are toluene, carbon tetrachloride, benzene, trichloroethane, and trichloroethylene.

The asymmetric esterification of this invention is preferably carried out in a reaction system containing water in an amount as small as possible or containing substantially no water in order to proceed the reaction with high efficiency, because the presence of a much amount of water inhibits the proceeding of the esterification reaction.

The optically active 3-phenylglycidic acid esters (I) thus produced can be isolated and collected from the reaction mixture by the following method.

Since an alkali metal salt (e.g. sodium salt) of unreacted 3-phenylglycidic acid (II) has less solubility in an organic solvent and has higher solubility in water in comparison with the produced optically active 3-phenylglycidic acid ester (I), the reaction mixture is mixed with an aqueous alkali solution (e.g. aqueous sodium hydrogen carbonate solution), by which the unreacted compound (II) is moved to the aqueous phase, and then, if desired, an aqueous sodium hydrogensulfite solution is further added to the mixture, by which the decomposed products of the substrate compounds are also moved to the aqueous phase. Thereafter, the organic solvent layer is separated, concentrated under reduced pressure, and then the product is recrystallized from an appropriate solvent (e.g. n-hexane) to give the desired optically active 3-phenylglycidic acid ester (I) as crystals.

The optically active 3-phenylglycidic acid esters (I) obtained by the above process of this invention can be converted into the desired pharmaceutically active 1,5-benzothiazepine derivatives. For instance, (2S, 3R)-3-(4-methylphenyl)glycidic acid alkyl ester can be converted into (−)-cis-2-(4-methylphenyl)-3-acetyloxy-5-[2-(dimethylamino)ethyl]-8-methyl-2,3-dihydro-1,5-benzothiazepin-4(5H)-one or a pharmaceutically acceptable salt thereof which has excellent platelet aggregation inhibitory activity. Said conversion can be carried out according to a known process as described in U.S. Pat. Nos. 4,567,175 and 4,590,188 the contents of which are hereby incorporated by reference.

The starting racemic trans-3-phenylglycidic acids (II) can easily be prepared by hydrolyzing the corresponding methyl ester of said compounds.

EXAMPLES

This invention is illustrated by the following Examples and Reference Examples but should not be construed to be limited thereto.

EXAMPLE 1

To a suspension of Lipase OF (origin: *Candida cylindracea*, manufactured by Meito Sangyo Co., Ltd., 5 g) in toluene (100 ml) were added (±)-trans-3-(4-methylphenyl)glycidic acid (0.5 g) and methanol (114 μl) in a 500 ml volume flask and the mixture was shaken at 30° C. for 24 hours at 300 r.p.m. After filtering off the enzyme, the reaction mixture was washed with an aqueous sodium hydrogen carbonate solution and an aqueous sodium hydrogensulfite solution, and the solvent was distilled off. The residue was crystallized by adding n-hexane thereto to give crude crystalline (2S, 3R)-3-(4-methylphenyl)glycidic acid methyl ester (60 mg). The crude crystals (60 mg) were recrystallized from n-hexane to give the desired (2S, 3R)-3-(4-methylphenyl)glycidic acid methyl ester (40 mg).

Figure 2:
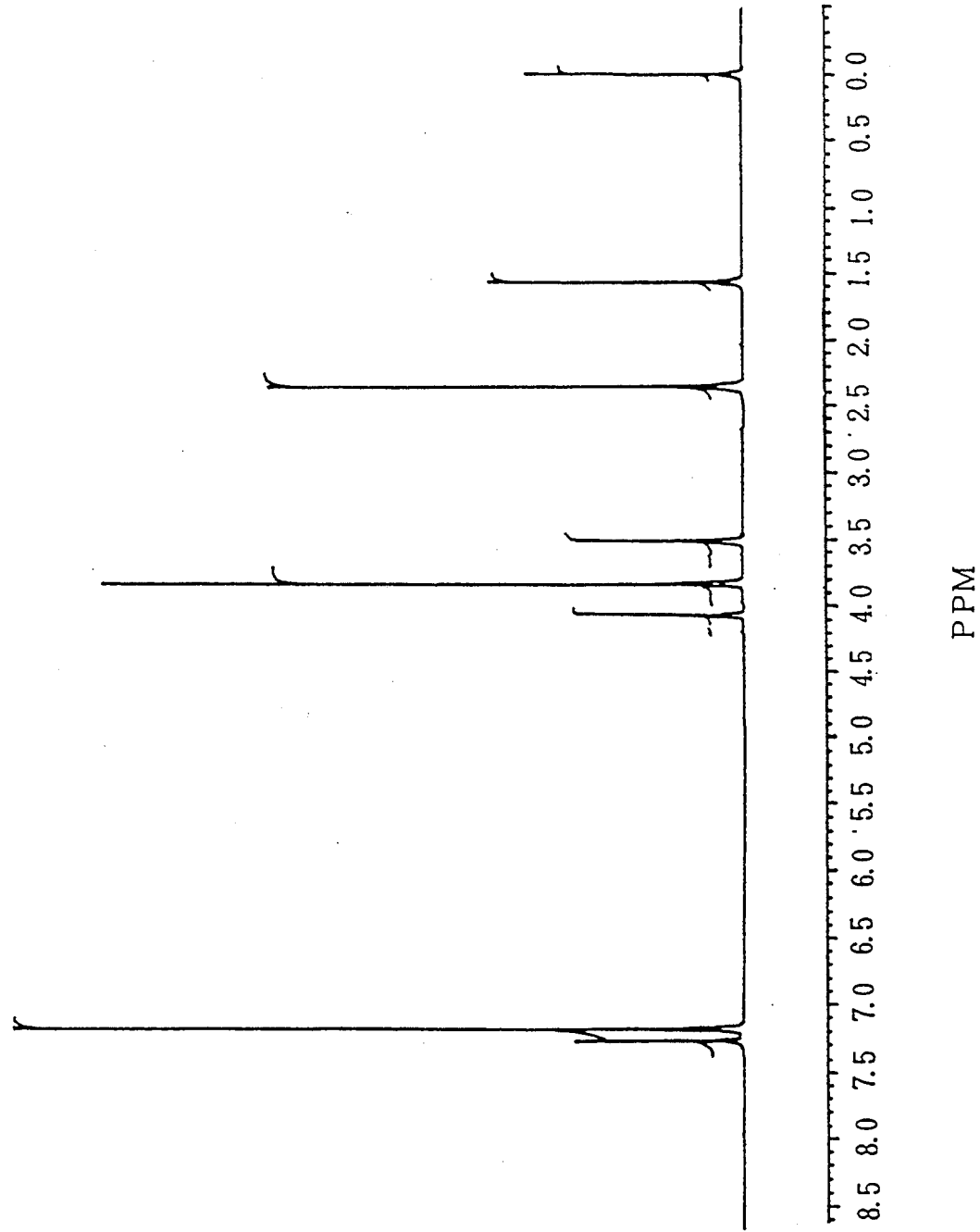
FIG. 2 shows NMR spectrum of (2S, 3R)-3-(4-methylphenyl)glycidic acid methyl ester obtained in Example 1.
Figure 3:
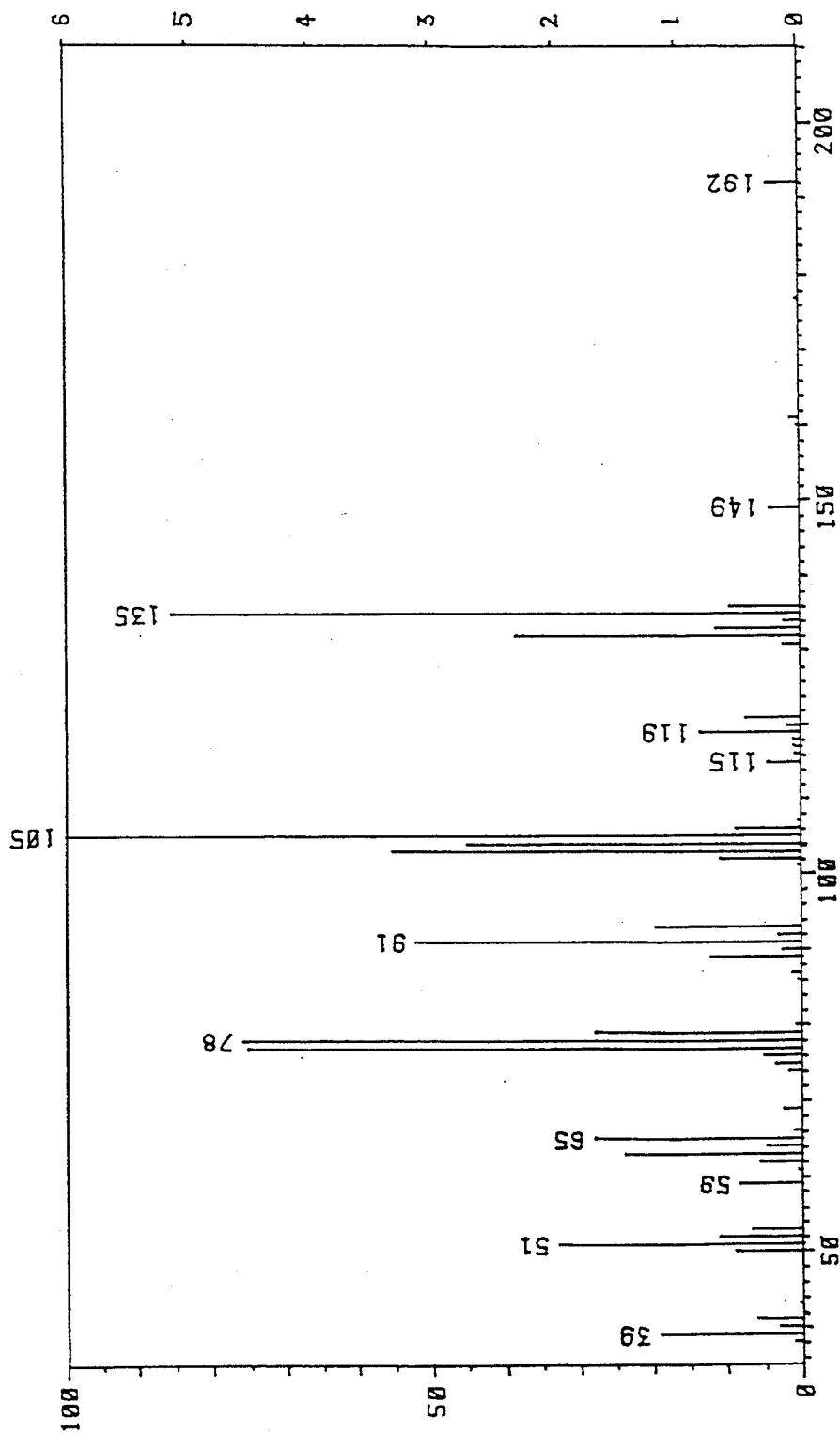
FIG. 3 shows Mass spectrum of (2S, 3R)-3-(4-methylphenyl)glycidic acid methyl ester obtained in Example 1.

M.p.: 50° C. $[\alpha]_D^{20}$: +207° (c=0.2, methanol) Optical purity: >99% IR spectrum: shown in the accompanying FIG. 1 NMR spectrum: shown in the accompanying FIG. 2 Mass spectrum: shown in the accompanying FIG. 3

Example 2

A suspension of an enzyme as shown in the following Table 1 (50 mg) in toluene (1.0 ml), (±)-trans-3-(4-methylphenyl)glycidic acid (5.0 mg) and methanol (1.14 μl) were added into a test tube (outer diameter, 13 mm), and the mixture was shaken at 30° C. for 24 hours at 300 r.p.m. The resulting reaction mixture contained (2S, 3R)-3-(4-methylphenyl)glycidic acid methyl ester in the amount as shown in the following Table 1. The enantiomer (2R, 3S) isomer was almost not observed in the reaction mixture.

The measurement of the content of the optically active compound in the above example and also other examples hereinafter was carried out by high performance liquid chromatography with Chiralcel OJ ($\phi$ 4.6×250 mm, manufactured by Daicel Chemical Industries, Ltd., Japan).

TABLE 1

| Enzymes used (50 mg/ml) | Content of (2S, 3R) isomer (mg/ml) |
|---|---|
| Lipase OF (origin: *Candida cylindracea*, manufactured by Meito Sangyo Co., Ltd.) | 0.80 |
| Lipase MY (origin: *Candida cylindracea*, manufactured by Meito Sangyo Co., Ltd.) | 0.24 |

TABLE 1-continued

| Enzymes used (50 mg/ml) | Content of (2S, 3R) isomer (mg/ml) |
|---|---|
| Lipase AY (origin: *Candida cylindracea*, manufactured by Amano Pharmaceutical Co., Ltd.) | 0.12 |
| Lipase M (origin: *Mucor javanicus*, manufactured by Amano Pharmaceutical Co., Ltd.) | 0.07 |
| Esterase (origin: *Mucor miehei*, manufactured by Gist) | 0.50 |
| Lipase (origin: *Rhizopus chinensis*, manufactured by Snow Brand Milk Products Co., Ltd., Japan) | 0.18 |
| Lipase YS (origin: Pseudomonas sp., manufactured by Amano Pharmaceutical Co., Ltd.) | 0.06 |
| Lipase CES (origin: Pseudomonas sp., manufactured by Amano Pharmaceutical Co., Ltd.) | 0.06 |
| Esterase SM (produced by lyophilizing the culture supernatant of *Serratia marcescens* FERM BP-487) | 0.30 |

Example 3

To a suspension of Lipase OF (origin: *Candida cylindracea*, manufactured by Meito Sangyo Co., Ltd., 50 mg) in an organic solvent (1.0 ml) as shown in the following Table 2 were added ($\pm$)-trans-3-(4-methylphenyl)glycidic acid (5.0 mg) and methanol (1.14 µl) in a test tube (outer diameter, 13 mm), and the mixture was shaken at 30° C. for 24 hours at 300 r.p.m. The resulting reaction mixture contained (2S, 3R)-3-(4-methylphenyl)glycidic acid methyl ester in the amount as shown in the following Table 2.

TABLE 2

| Organic solvents | Content of (2S, 3R,) isomer (mg/ml) |
|---|---|
| Toluene | 0.80 |
| Benzene | 1.01 |
| Carbon tetrachloride | 0.82 |
| Trichloroethane | 1.19 |
| Trichloroethylene | 1.25 |
| Hexane | 0.33 |
| Heptane | 0.44 |
| Cyclohexane | 0.42 |
| Isooctane | 0.34 |
| Chloroform | 0.49 |

Example 4

To a suspension of Lipase OF (origin: *Candida cylindracea*, manufactured by Meito Sangyo Co., Ltd.) of the amount as shown in the following Table 3 in toluene (1.0 ml) were added ($\pm$)-trans-3-(4-methylphenyl)glycidic acid (5.0 mg) and methanol (1.14 µl) in a test tube (outer diameter, 13 mm), and the mixture was shaken at 30° C. for 24 hours at 300 r.p.m. The resulting reaction mixture contained (2S, 3R)-3-(4-methylphenyl)glycidic acid methyl ester in the amount as shown in the following Table 3.

TABLE 3

| Amount of Lipase OF (mg/ml) | Content of (2S, 3R) isomer (mg/ml) |
|---|---|
| 5 | 0.13 |
| 10 | 0.34 |
| 25 | 0.69 |
| 50 | 0.80 |

TABLE 3-continued

| Amount of Lipase OF (mg/ml) | Content of (2S, 3R) isomer (mg/ml) |
|---|---|
| 100 | 1.10 |
| 200 | 0.70 |

Example 5

To a suspension of Lipase OF (origin: *Candida cylindracea*, manufactured by Meito Sangyo Co., Ltd., 50 mg) in toluene (1.0 ml) were added ($\pm$)-trans-3-(4-methylphenyl)glycidic acid (MPGA) and methanol (MA) in the concentrations as shown in the following Table 4 respectively in a test tube (outer diameter, 13 mm), and the mixture was shaken at 30° C. for 24 hours at 300 r.p.m. The resulting reaction mixture contained (2S, 3R)-3-(4-methylphenyl)glycidic acid methyl ester in the amount as shown in the following Table 4.

TABLE 4

| Concentration of the substrates | | Content of (2S, 3R) isomer (mg/ml) |
|---|---|---|
| MPGA (mg) | MA (µl) | |
| 1.0 | 0.29 | 0.15 |
| 2.5 | 0.57 | 0.40 |
| 5.0 | 0.29 | 0.38 |
| 5.0 | 0.57 | 0.65 |
| 5.0 | 1.14 | 0.80 |
| 10.0 | 2.28 | 1.44 |
| 25.0 | 5.70 | 1.35 |
| 50.0 | 11.40 | 1.30 |
| 100.0 | 22.80 | 1.12 |

Example 6

Lipase participates in hydrolysis of esters and also in the reverse reaction, i.e. synthesis of esters, and these both actions are in the equilibrium in the reaction system, which is largely influenced by the water content of the reaction system.

From this viewpoint, the correlation between the water content of the reaction system and the ratio of synthesis of esters was investigated as follows.

To a toluene solvent (1.0 ml) containing water in the amount as shown in the following Table 5 were added Lipase OF (origin: *Candida cylindracea*, manufactured by Meito Sangyo Co., Ltd., 50 mg), ($\pm$)-trans-3-(4-methylphenyl)glycidic acid (5.0 mg) and methanol (1.14 µl) in a test tube (outer diameter, 13 mm), and the mixture was shaken at 30° C. for 24 hours at 300 r.p.m. As a result, the reaction mixture contained (2S, 3R)-3-(4-methylphenyl)glycidic acid methyl ester in the amount as shown in the following Table 5.

TABLE 5

| Water content | Content of (2S, 3R) isomer (mg/ml) |
|---|---|
| Completely dehydrated toluene (drained with molecular sieves) | 1.15 |
| Commercially available highest grade of toluene | 0.82 |
| Toluene saturated with water | 0.80 |
| Toluene containing 0.1 ml of water | 0 |
| Toluene containing 0.5 ml of water | 0 |

Example 7

To a suspension of Lipase OF (origin: *Candida cylindracea*, manufactured by Meito Sangyo Co., Ltd., 50 mg) in toluene (1.0 ml) were added (±)-trans-3-(4-methylphenyl)glycidic acid (5.0 mg) and an equimolar amount of an alkanol as shown in the following Table 6 in a test tube (outer diameter, 13 mm), and the mixture was shaken at 30° C. for 24 hours at 300 r.p.m. The resulting reaction mixture contained (2S, 3R)-3-(4-methylphenyl)glycidic acid methyl ester in the amount as shown in the following Table 6.

TABLE 6

| Alkanols | Content of (2S, 3R) isomer (mg/ml) |
|---|---|
| Methyl alcohol | 0.80 |
| Ethyl alcohol | 1.16 |
| n-Propyl alcohol | 1.25 |
| n-Amyl alcohol | 0.91 |
| n-Octyl alcohol | 0.48 |

Usefulness of the Invention

The process of this invention can provide the desired optically active 3-phenylglycidic acid esters from the racemic trans-3-phenylglycidic acids in a single step, whereby the product can be obtained in a highly pure form. Accordingly, the process of this invention is useful for the preparation of the optically active 3-phenylglycidic acid esters on an industrial scale.

What is claimed is:

1. A process for preparing an optically active (2S, 3R) 3-phenylglycidic acid ester of the formula:

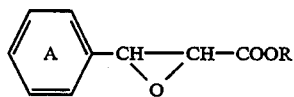
(I)

wherein the ring A is a phenyl ring which has a lower alkyl group as a substituent and R is an alkyl group, which comprises treating a racemic trans-3-phenylglycidic acid of the formula:

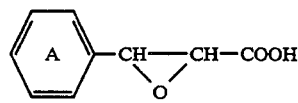
(II)

wherein the ring A is as defined above, and an alkanol in an organic solvent with a hydrolase which preferentially esterifies of the (2S, 3R) isomer of said racemic 3-phenylglycidic acid, said hydrolase being produced by a microorganism of the genus Candida, Mucor, Rhizopus, Pseudomonas or Serratia, and isolating and collecting the resulting optically active 3-phenylglycidic acid ester from the reaction mixture.

2. The process according to claim 1, wherein the optically active ester to be isolated is (2S, 3R)-3-(4-methylphenyl)glycidic acid alkyl ester.

3. The process according to claim 1, wherein the isolation and collection of the desired optically active ester is carried out by adding an aqueous alkali solution to the reaction mixture to move the unreacted enantiomer to the aqueous phase, separating the organic layer, and removing the organic solvent from the organic layer.

4. The process according to claim 1, wherein the organic solvent is an organic solvent which dissolves (2S, 3R)-3-(4-methylphenyl)glycidic acid alkyl ester but is substantially immiscible with water.

5. A process for preparing a 1,5-benzothizepine derivative, which comprises treating a racemic trans-3-(4-methylphenyl)glycidic acid and an alkanol in an organic solvent with a hydrolase having an ability of preferential esterification of the (2S, 3R) isomer of said racemic 3-phenylglycidic acid, said hydrolase being a hydrolase produced by a microorganism of the genus Candida, Mucor, Rhizopus, Pseudomonas or Serratia, isolating and collecting the resulting (2S, 3R)-3-(4-methylphenyl)glycidic acid alkyl ester from the reaction mixture, and converting said ester into (−)-cis-2-(4-methylphenyl)-3-acetyloxy-5-(2-(dimethyl-amino)ethyl)-8-methyl-2,3-dihydro-1,5-benzothiazepin-4(5H)-one or a pharmaceutically acceptable salt thereof.

* * * * *